US010229500B2

(12) United States Patent
Gibby et al.

(10) Patent No.: US 10,229,500 B2
(45) Date of Patent: Mar. 12, 2019

(54) INCORPORATION OF STATISTICAL STRENGTH INTO VOXELS IN AN FMRI IMAGE

(71) Applicant: Novarad Corporation, American Fork, UT (US)

(72) Inventors: Wendell Arlen Gibby, Mapleton, UT (US); Steven Todd Cvetko, Draper, UT (US); Long Nguyen, Salt Lake City, UT (US)

(73) Assignee: Novarad Corporation, American Fork, UT (US)

( * ) Notice: Subject to any disclaimer, the term of this patent is extended or adjusted under 35 U.S.C. 154(b) by 0 days.

(21) Appl. No.: 15/465,442

(22) Filed: Mar. 21, 2017

(65) Prior Publication Data
US 2018/0276820 A1 Sep. 27, 2018

(51) Int. Cl.
G06T 7/00 (2017.01)
(52) U.S. Cl.
CPC .. *G06T 7/0014* (2013.01); *G06T 2207/10088* (2013.01); *G06T 2207/30016* (2013.01)
(58) Field of Classification Search
CPC ................. G01R 33/00; A61B 5/00
USPC .................. 382/128–134
See application file for complete search history.

(56) References Cited

U.S. PATENT DOCUMENTS 8,886,283 B1 * 11/2014 Chen ............... A61B 5/055
382/128
8,965,093 B2 * 2/2015 Fan ............... G06T 7/0012
382/131

* cited by examiner

Primary Examiner — Abolfazl Tabatabai
(74) Attorney, Agent, or Firm — Thorpe North & Western, LLP

(57) ABSTRACT

Technology is described for incorporating statistical strength from neighboring voxels in an fMRI image. The method can include the operation of capturing an fMRI image of a human organ and the fMRI image includes statistical values for voxels in order to detect changes associated with blood flow representing organ activity. The statistics of the fMRI image can be upsampled to a larger coordinate size. Another operation can be resampling the statistical values of the fMRI image to improve the statistical strength for target voxels in the fMRI by identifying strong statistical values in neighboring voxels in a defined neighborhood of the target voxels and improving statistical values of the target voxels using the strong statistical values. The statistics of the fMRI image can integrated into a region of interest identified for the human organ to improve data values of the target voxels while retaining regional boundaries.

20 Claims, 8 Drawing Sheets

INCORPORATION OF STATISTICAL STRENGTH INTO VOXELS IN AN FMRI IMAGE

BACKGROUND

Magnetic resonance imaging (MRI) may be used to form images of the brain's anatomy and the physiological processes of the brain. MRI brain scans can use a strong, permanent and static magnetic field to align nuclei in the brain region being studied. Another magnetic field, the gradient field, is then applied to spatially locate different nuclei. Finally, a radio frequency (RF) pulse is generated to kick the nuclei to higher magnetization levels, with the resulting effect depending on where they are located. When the RF field is removed, the nuclei go back to their original states, and the energy the nuclei emit is measured with a coil to recreate the positions of the nuclei. MRI thus provides a static imaged view of the brain tissue.

Functional magnetic resonance imaging or functional MRI (fMRI) is a functional brain imaging procedure using MRI (magnetic resonance imaging) technology that measures brain activity by detecting changes associated with blood flow. This technique relies on the fact that cerebral blood flow and neuronal activation are coupled. When an area of the brain is in use, blood flow to that region tends to increase.

fMRI can use the properties of oxygen-rich blood in imaging. The central thrust behind fMRI may extend MRI to capture functional changes in the brain caused by neuronal activity. Differences in magnetic properties between arterial (oxygen-rich) and venous (oxygen-poor) blood can provide this information because changes in blood flow and blood oxygenation in the brain may be linked to neural activity.

One form of fMRI uses the blood-oxygen-level-dependent (BOLD) contrast method. This is a type of specialized brain scan used to map neural activity in the brain by imaging the change in blood flow (hemodynamic response) related to energy use by brain cells. In recent decades, fMRI has come to dominate brain mapping technology because fMRI does not use invasive medical procedures on patients (e.g., shots, surgery, ingested substances, or exposure to radiation, etc.). Other methods of obtaining contrast are arterial spin labeling and diffusion MRI. The latter procedure is similar to MRI but uses the change in magnetization between oxygen-rich and oxygen-poor blood as its basic measure. This measure is frequently corrupted by noise from various sources and hence statistical procedures are used to extract the underlying signal. The resulting brain activation can be presented graphically by coding the strength of activation across the brain or the region studied. The technique can localize activity to within millimeters but, typically, no better than within a window of a few seconds.

DETAILED DESCRIPTION

A technology is provided for improving the fidelity and precision of statistical t-maps used to display the functional activity of a human patient's brain by utilizing existing statistical techniques combined with statistical strengthening of voxel data as the voxel data is upsampled to a larger image size. In one example, cubic spline interpolation of the voxel data or statistical data may be used to improve and/or identify voxel values for target voxels in the upsampled image of the brain activity. This procedure borrows strength from the neighboring voxels to attenuate (correlated) noise effects while retaining regional boundaries. The procedure also entails both an interpolation between the in-slice data voxels and a cubic spline interpolation in three dimensions (e.g., across slices) looking at averages from 64 adjacent voxels. The probability of true activation for a voxel is increased when a majority of adjacent voxels are also activated. When the present technology is compared against the statistical t-value display maps of data sets processed by SPMa (an existing processing system for fMRI) and the same data set processed with existing statistical tools (utilizing random field theory, Gaussian Smoothing, and REML) and using the present technology, the present technology provides a significant improvement to the subject fMRI images of a human patient.

fMRI is a highly promising technology for evaluation of brain injury, psychiatric illnesses, and dementia. Unfortunately, activation of the brain can be noise limited. Even with the most advanced technology available today, functional MRI (fMRIs) may still be noise limited. Echo planar imaging used to improve temporal resolution in the evaluation of subtle changes in deoxyhemoglobin levels with brain activation may be considered one statistical step above guessing. Modern fMRI depends on sophisticated statistical tools such as random field theory and Restricted Maximum Likelihood (REML) techniques to tease out subtle distinctions between noise and true brain activity. Existing techniques of smoothing of these fMRI images using known filtering methods do not yield additional information density but rather "average out" or blur the noise already present. This technology helps overcome the problems created with simply filtering the statistical data that exists in the fMRI image. More specifically, this technology can make an improvement in the statistical quality of the data, which in turn can make a significant contribution to the reliability and clinical confidence of the data.

Figure 1:
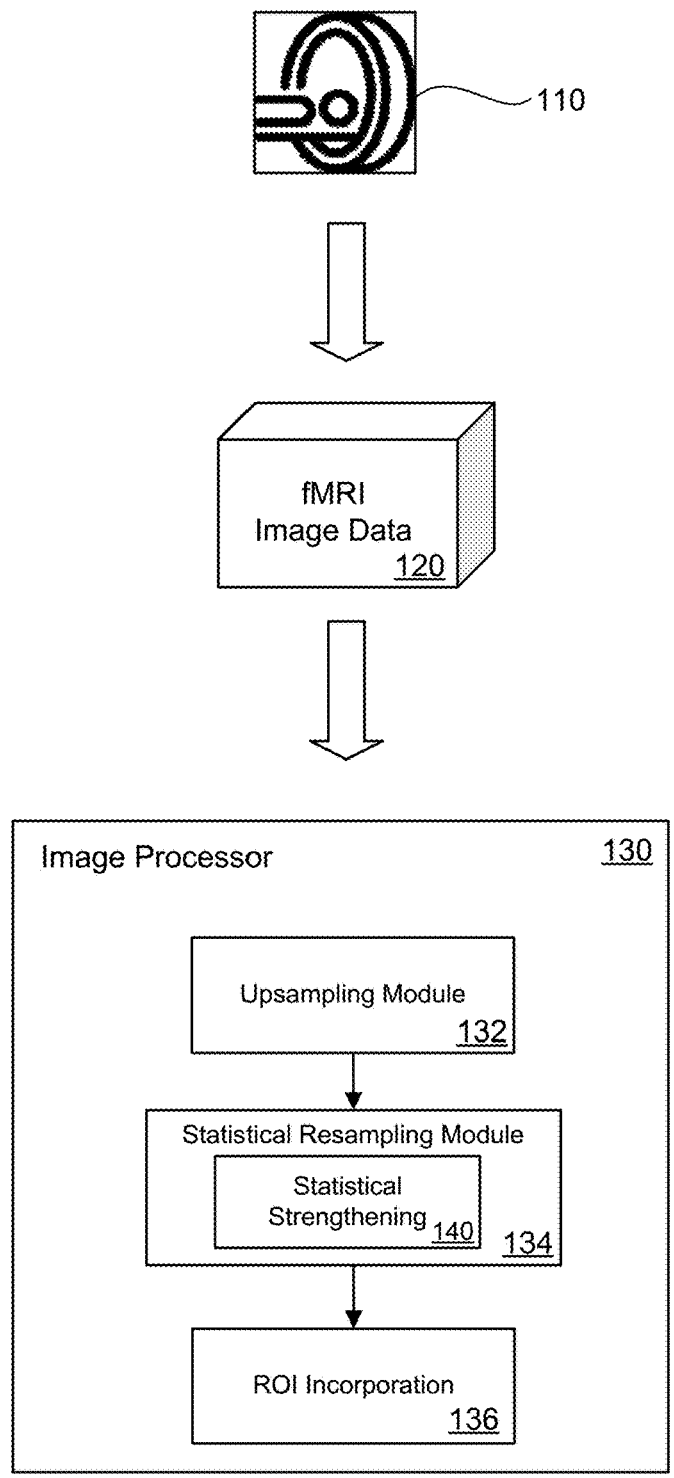
FIG. 1 is a block diagram illustrating an example of a system for incorporating statistical strength into voxels in an fMRI image.

FIG. 1 illustrates a system for capturing and strengthening an fMRI image or data set for a human brain representing brain activity by detecting changes associated with blood flow. Specifically, statistical strength can be incorporated into the voxels of an fMRI image. Initially, an fMRI image can capture activity in a human brain and the image may have voxels with statistical values or t-values representing brain activity by identifying changes associated with blood flow. An MRI machine 110 or device may be used to capture the fMRI image 120. The capturing of the statistical values to form a statistical parametric map (SPM) may use the parametric method to identify t-values that exceed a statistical threshold of significance over a time based window. In an alternative configuration the "known parametric method" may be used to capture the statistical values for voxels or t-values.

The image captured may be an fMRI image that is 64 by 64 voxels in size, for example. Since this image is desired to be overlaid on or combined with an anatomical image that is an average anatomical image, then the fMRI image may be increased in size to allow the FMRI image to be accurately overlaid on the anatomical image. The anatomical image may be, for example, 512 voxels by 512 voxels. Thus, the 64 by 64 image may be upsampled to 512 by 512 or some size that fits appropriately within the larger image. While 64 by 64 and 512 by 512 are given as example reference sizes, the sizes of the fMRI images may range from 3 by 3 grids up to grids that are measured by the hundreds, thousands or even millions of voxels, as the fMRI and MRI imaging process may support.

The fMRI image may be sent to an image processor 130 to be upsized and further processed for viewing by medical personnel. The image processor may be an image processor 130 that is located on a server separate from MRI machine 110 or the image processor 130 may be on a client machine separate from the MRI machine 110 where the fMRI images are viewable by a user, a doctor, medical personnel, or an administrator. The statistics of the fMRI image may be upsampled to a larger coordinate size (e.g., from 64×64 to 512×512) using an upsampling module, and this upsampling operation can result in voxels without statistical values in the fMRI image.

A further operation performed by the statistical resampling module 134 of the technology is the sampling or resampling of the statistics of the fMRI image to improve the statistical strength 140 for target voxels (i.e., target statistics) in the fMRI image for selected voxels in a defined neighborhood. The statistics can be sampled or re-sampled in a statistical way that can provide accurate voxels values that are "filled into" the larger image without spreading an undue amount of existing noise throughout the image, and the existing voxel values may be strengthened. In one example configuration, zero values or approximated place holder values may be filled into the fMRI image.

During the resampling operation, the target voxels (i.e., statistical values) can be modified by adjusting the value of the target voxels by determining that selected voxels in a neighborhood of interest are statistically likely to be related to the target voxels. The target voxels may be modified by increasing the value of target voxels by determining that voxels in a neighborhood of interest are statistically likely to increase the value of the target voxels. Alternatively, the target voxels may be modified by decreasing the value of the target voxels by determining that voxels in a neighborhood of interest are statistically likely to decrease the value of the target voxels.

In one example of statistical strengthening, the statistical values of the fMRI image can be resampled using cubic interpolation of the voxels in a region near each of the target voxels. The value of target voxels can be modified with cubic interpolation using the values of, for example, 64 neighbor voxels in three dimensions. While the number 64 has provided as an example of neighbor voxels that may be used in cubic interpolation, varying numbers of voxels may be picked that surround a voxel in three dimensions for use in a cubic spline interpolation. The voxels selected to be used in the cubic interpolation may be directly adjacent to one another and the target voxels. Alternatively, the voxels may be selected in a screen door type of pattern or an irregular pattern, as may be useful. Similarly, the cubic splines that are computed may be in three axes orthogonal to faces of the voxels or the cubic splines may also be computed along any axis with the voxels. For example, the cubic splines may be computed in line with axes through the vertices joining faces of a voxel, in line with axes through the corners of the voxels or any other axes. In addition, the voxels may be on any shape that is three dimensional include cube shaped, rectangular shaped, polygon shaped or other shapes. More specifically, in three dimensions, 16 cubic spline calculations may be made for each voxel. The location of the target voxel in the cubic splines may also vary and may be at the ends, center or other points on the cubic spline.

The upsampled image with the resampled statistics of the fMRI image may then be integrated into the appropriate region of interest identified in an image of the human brain. This operation may be performed by a ROI (region of interest) incorporation module 136. More specifically, an anatomical image of the brain can be identified (e.g., a 512×512 image) and this anatomical image may come from a composite of control MRI images from control test subjects or the anatomical image may be a modeled anatomical image.

The fMRI image that has been upsampled may be overlaid on or composited with the anatomical image of the brain. This composite image enables the comparison of the higher resolution brain anatomy image with the lower resolution fMRI image in upsized and resampled form. This comparison can aid a medical professional in diagnosing whether there are medical issues that are identifiable using the upsized and resampled fMRI image.

The fMRI image may also have colors applied to voxels in the fMRI image. The colors may be applied to statistical value groups or classes in the fMRI image or to individual statistical values in the fMRI image.

The data values used in the upsized and resampled fMRI images may be improved up to 25% with this technique. Cubic spline interpolation yields a significant incremental step forward in producing higher quality statistical fMRI maps or t-maps in a medical diagnostic environment which is very signal limited. This improved result is due in part to the use of a significant number of voxel values used in cubic interpolation and the cubic calculations that can more accurately be fit to the available voxels, which in turn may produce better interpolations to identify additional voxels or correct existing voxels.

Figure 2:
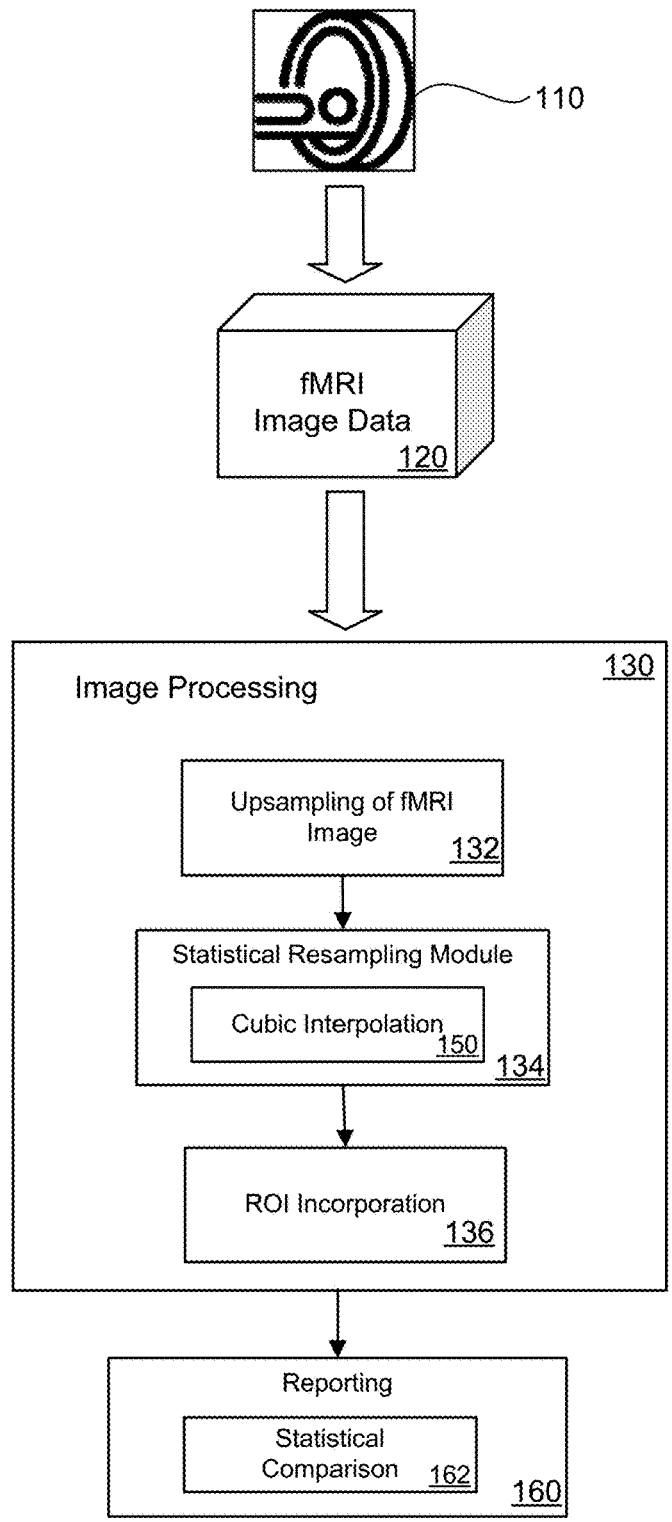
FIG. 2 is a block diagram illustrating an example of a system for incorporating statistical strength into voxels in an fMRI image using cubic spline interpolation.

FIG. 2 illustrates a block diagram with a system for incorporating statistical strength into voxels of an fMRI image. Specifically, resampling the statistical values of the fMRI image can occur using cubic interpolation 150 of the voxels in a region near each of the target voxels. The remaining operations illustrated in blocks 110, 120, 130, 132, 134 and 136 in FIG. 2 can be the same as FIG. 1.

A reporting operation may also be included, using a reporting module 160 which indicates when a subject fMRI image has been calculated as being outside a statistical measure of comparison. Specifically, the statistical comparison module 162 can determine whether the subject fMRI image is outside one, two or three standard deviations of variation from a control group of fMRI images and report that a statistical deviation that may exist.

In an alternative configuration, a statistically significant deviation measure for an fMRI image can be computed, as compared to control group fMRI data. This statistically significant deviation measure may be created by taking X number of reference fMRI images for a control group (e.g., 10-200 reference images) and generating N number of random images (e.g., 1000-5000) or permutation images from the statistical values for each reference image and using the X*N number of images as the total control group for the statistical calculation. Then the subject fMRI image may be statistically compared to the randomized control group. If the subject fMRI image is one or more standard deviations from the mean of the control group (e.g., in a normal distribution), then the deviation of a subject fMRI image can be considered to be statistically significant. The use of permutation testing enables a health care provider to know how statistically significant the difference between the patient's fMRI is from a control group of fMRIs.

Figure 3A:
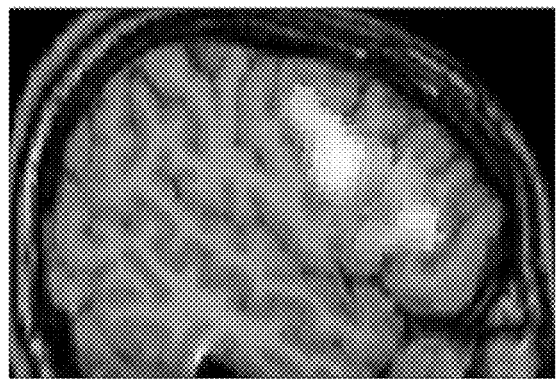
FIG. 3a is an image of a brain and statistical values from an fMRI image illustrating the brain activation without any statistical strengthening of the statistical values.
Figure 3B:
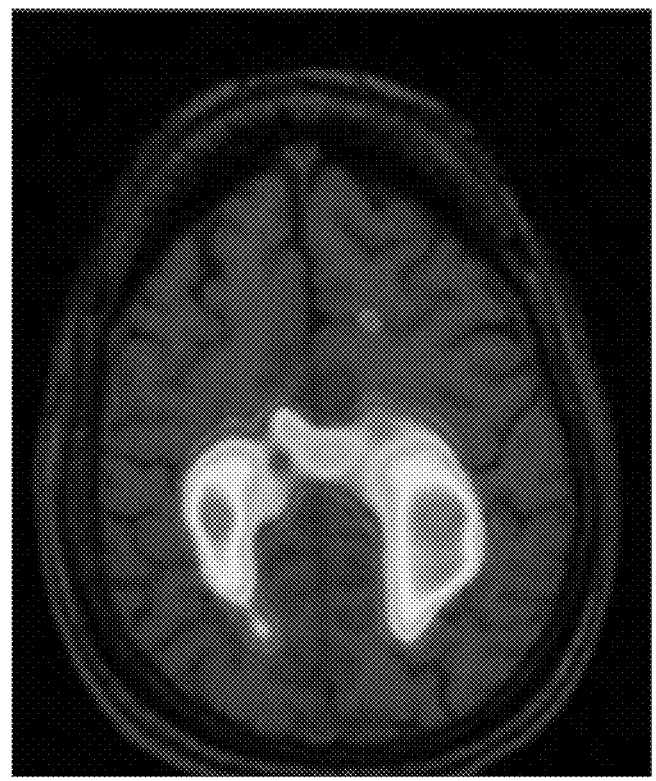
FIG. 3b is an image of a brain and statistical values from an fMRI image illustrating the brain activation with statistical strengthening of the statistical values.

FIG. 3a illustrates an fMRI image overlaid on or composited with a control anatomical image of a human brain where no statistical strengthening has taken place. FIG. 3b illustrates an fMRI image overlaid on a human brain after statistical strengthening has taken place and the fMRI image has been upsized to the same size as the anatomical reference image. In addition, colors can be assigned to the statistical values or statistical values ranges to provide a more granular colored view of the fMRI image that has been upsized and resampled.

Figure 4:
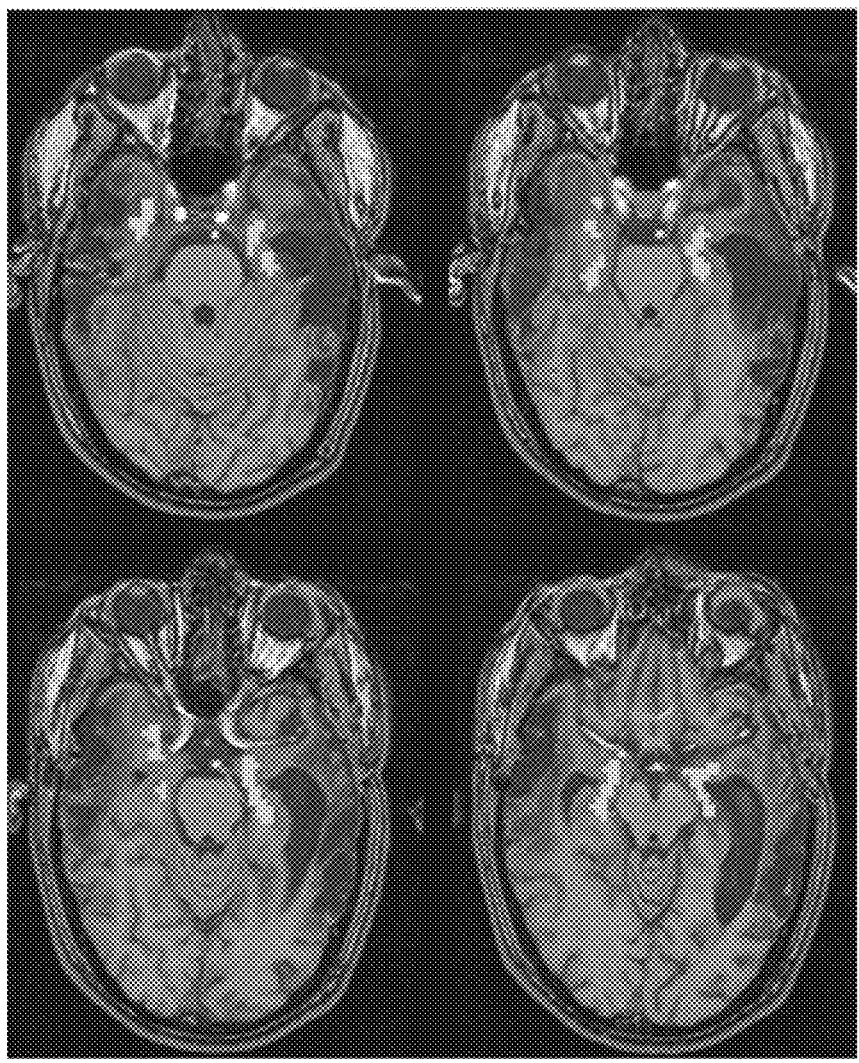
FIG. 4 illustrates image of brains and statistical values from fMRI images illustrating brain activation without any statistical strengthening of the statistical values.
Figure 5A:
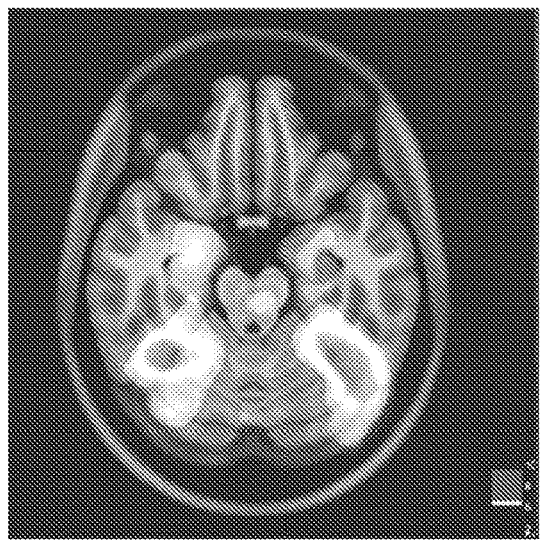
FIGS. 5a and 5b illustrate an image of a brain and statistical values from an fMRI image illustrating the brain activation with statistical strengthening of voxel values.
Figure 5B:
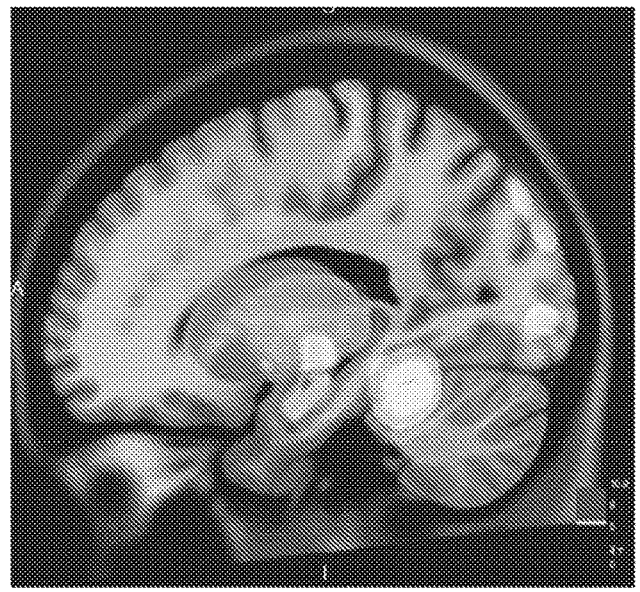

FIG. 4 illustrates an image of an fMRI image that is overlaid on an anatomical image of a human brain without any correction or improvement. FIGS. 5a and 5b illustrate fMRI images that have been statistically strengthened and have had color gradations added to the statistical values to more accurately illustrate the functional activity of the brain.

Figure 5C:
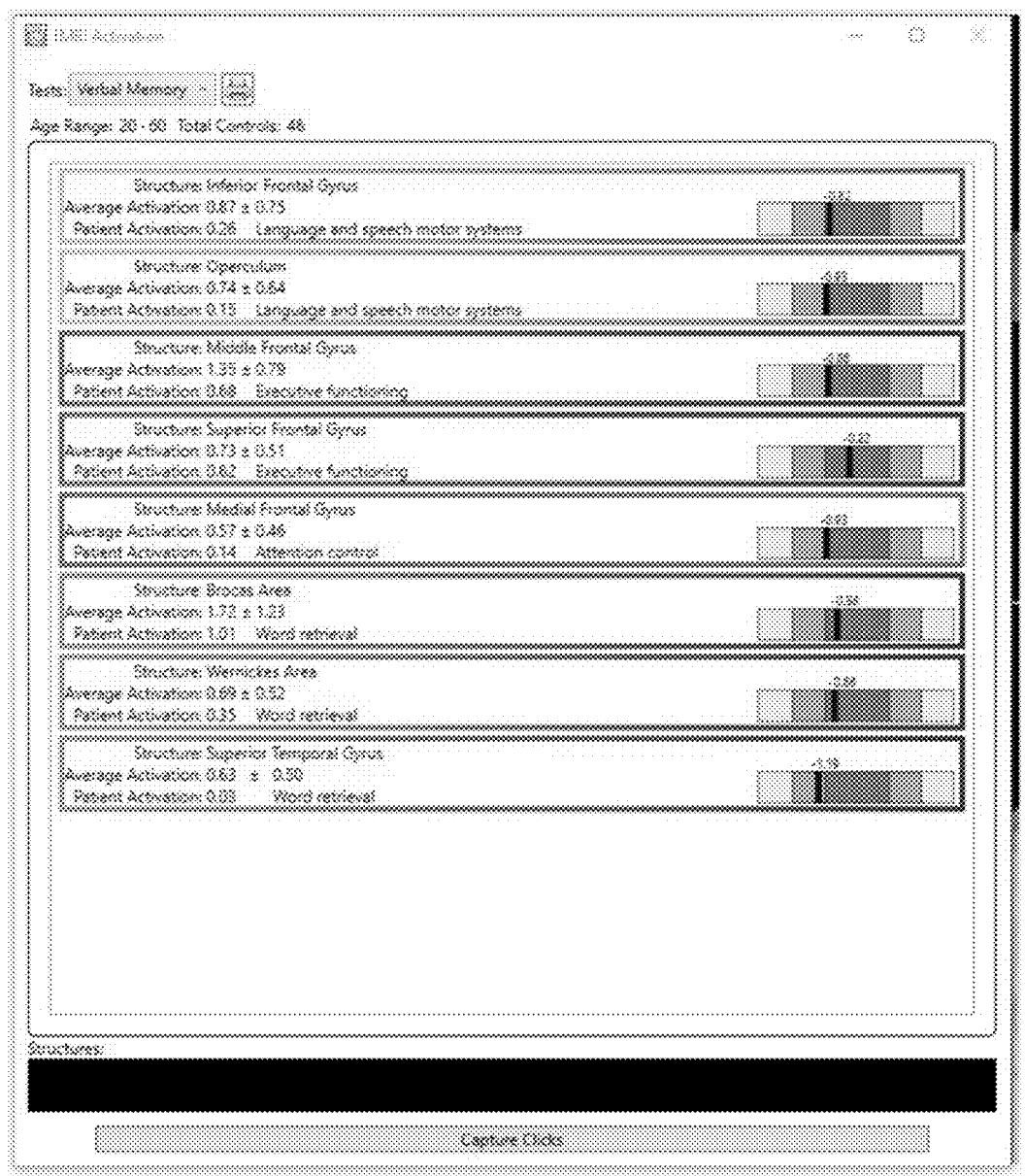
FIG. 5c illustrates reporting of statistical values for an fMRI evaluation.

FIG. 5c illustrates an example report of fMRI values that have been statistically strengthened by brain region. A patient's activation and average activation is also shown for a brain region.

Figure 6:
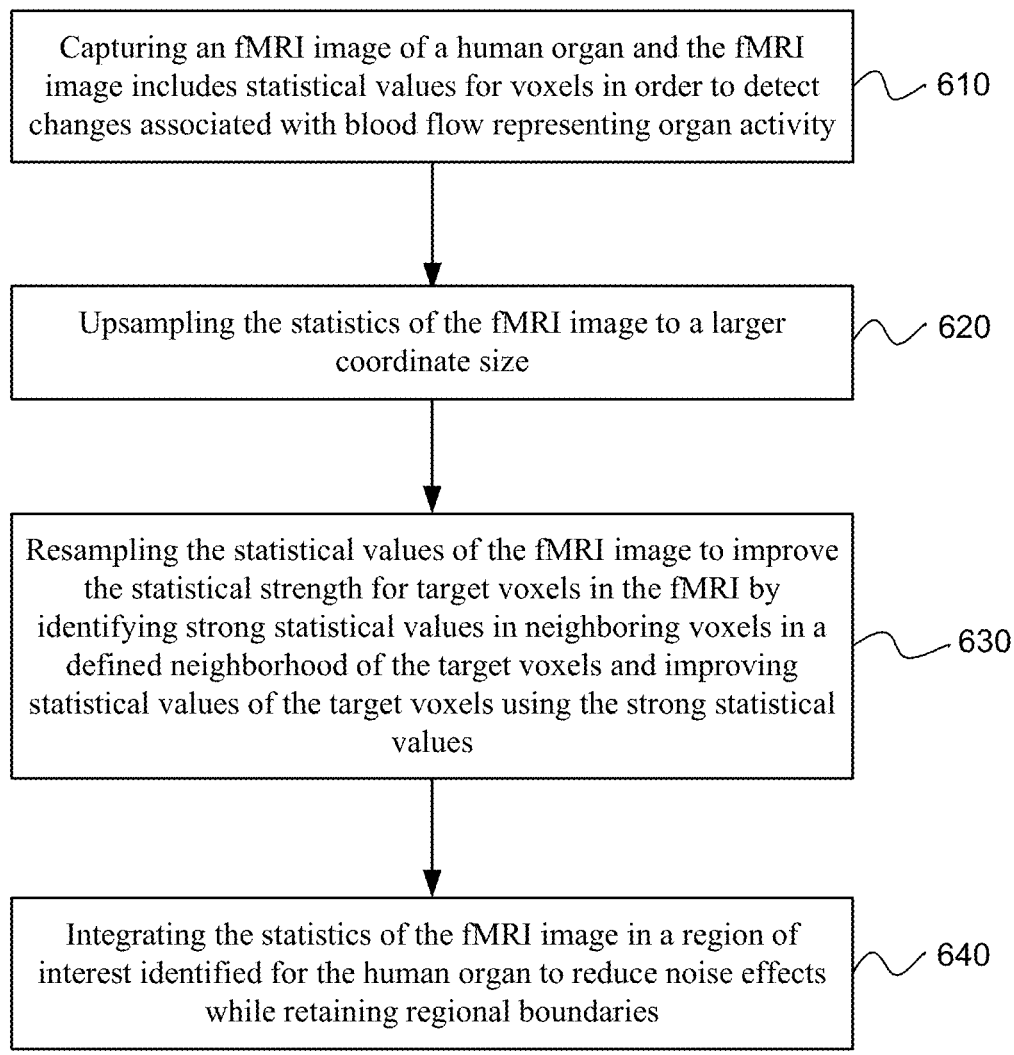
FIG. 6 illustrates a method for incorporating statistical strength into voxels in an fMRI image.

FIG. 6 illustrates a method for incorporating statistical strength from neighboring voxels into an fMRI image. An initial operation in the method is capturing an fMRI image of a human organ and the fMRI image includes statistical values for voxels in order to detect changes associated with blood flow representing organ activity, as in block 610. In one example, the organ may be the human brain. The statistics of the fMRI image can then be upsampled to a larger coordinate size, as in block 620.

The statistical values of the fMRI image can be resampled to improve the statistical strength for target voxels in the fMRI, as in block 630. The resampling can occur by identifying strong statistical values in neighboring voxels in a defined neighborhood of the target voxels and improving statistical values of the target voxels using the strong statistical values.

During the resampling operation, the target voxels can be modified by adjusting the value of the selected voxels by determining that selected voxels in a neighborhood of interest are statistically likely to be related to the selected voxels. The selected voxels may be modified by increasing the value of selected voxels by determining that voxels in a neighborhood of interest are statistically likely to increase the value of the selected voxels. Alternatively, the selected voxels may be modified by decreasing the value of selected voxels by determining that voxels in a neighborhood of interest are statistically likely to decrease the value of the selected voxels.

As described earlier, in one example of statistical strengthening, the statistical values of the fMRI image can be resampled using cubic interpolation of the voxels in a region near each of the target voxels. The value of selected voxels can be modified with cubic interpolation using the values of, for example, 64 neighbor voxels in three dimensions. While the number 64 has provided as an example of neighbor voxels that may be used in cubic interpolation, any number of voxels may be picked that surround a voxel for use in a cubic spline interpolation. The voxels selected to be used in the cubic interpolation may be directly adjacent to one another and the target voxels. Alternatively, the voxels may be selected in a screen door type of pattern in three dimensions or an irregular pattern in three dimensions.

Yet another operation can be integrating the statistics of the fMRI image in a region of interest identified for the human organ to improve data values of the target voxels while retaining regional boundaries, as in block 640. The operation of combining the fMRI image and the anatomical image of the human organ or brain may include identifying an anatomical image of the organ (e.g., a control image). Then the fMRI image that has been upsampled can be overlaid on the anatomical image of the organ in order to combine the images.

The statistics from the fMRI image and the fMRI image in visual form can then be displayed for medical diagnostic purposes. As described earlier, a subject fMRI image can be compared against reference group data created by a group of reference images. The technology may then report when a subject fMRI image is at least one standard deviation from an average of the reference group data.

Figure 7:
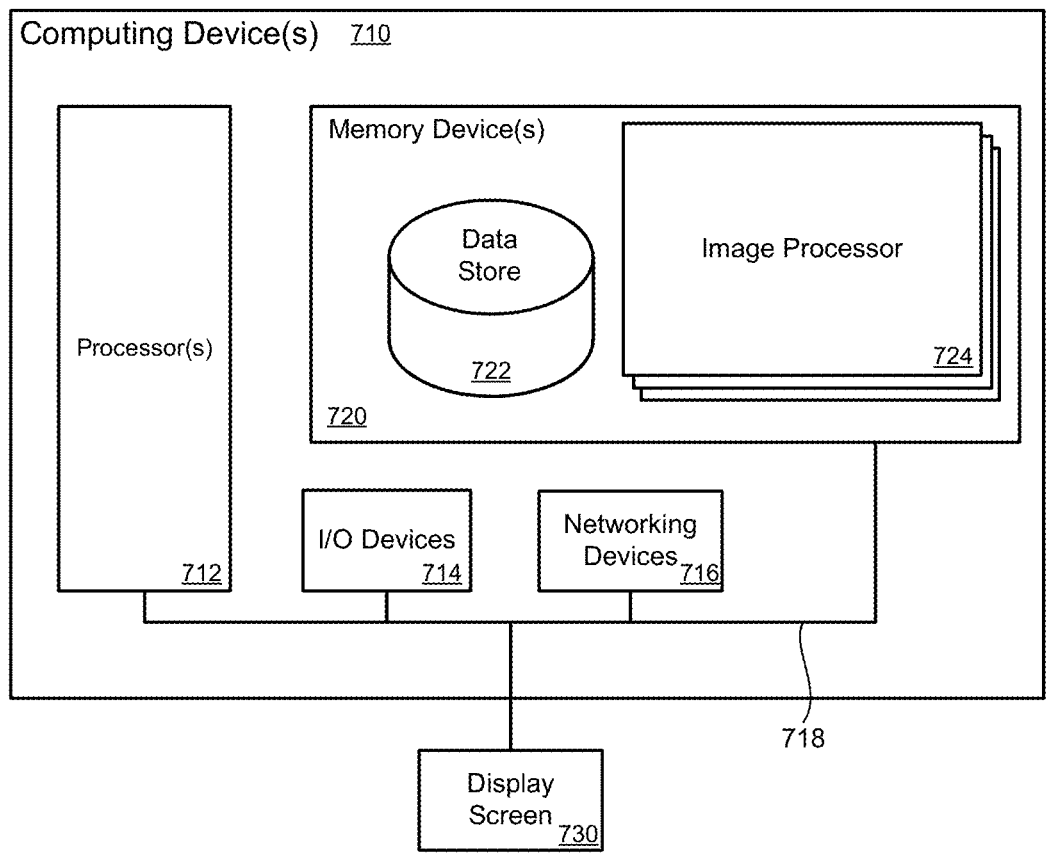
FIG. 7 is block diagram illustrating an example of a computing device for performing the computing and data storage functions of the present technology.

FIG. 7 illustrates a computing device 710 on which modules of this technology may execute. A computing device 710 is illustrated on which a high level example of the technology may be executed. The computing device 710 may include one or more processors 712 that are in communication with memory devices 720. The computing device may include a local communication interface 718 for the components in the computing device. For example, the local communication interface may be a local data bus and/or any related address or control busses as may be desired.

The memory device 720 may contain modules that are executable by the processor(s) 712 and data for the modules. Located in the memory device 720 are modules executable by the processor. For example, an image processor 724 and other modules may be located in the memory device 720. The modules may execute the functions described earlier. A data store 722 may also be located in the memory device 720 for storing data related to the modules and other applications along with an operating system that is executable by the processor(s) 712.

Other applications may also be stored in the memory device 720 and may be executable by the processor(s) 712. Components or modules discussed in this description that may be implemented in the form of software using high programming level languages that are compiled, interpreted or executed using a hybrid of the methods.

The computing device may also have access to I/O (input/output) devices 714 that are usable by the computing devices. An example of an I/O device is a display screen 730 that is available to display output from the computing devices. Other known I/O device may be used with the computing device as desired. Networking devices 716 and similar communication devices may be included in the computing device. The networking devices 716 may be wired or wireless networking devices that connect to the internet, a LAN, WAN, or other computing network.

The components or modules that are shown as being stored in the memory device 720 may be executed by the processor 712. The term "executable" may mean a program file that is in a form that may be executed by a processor 712. For example, a program in a higher level language may be compiled into machine code in a format that may be loaded into a random access portion of the memory device 720 and executed by the processor 712, or source code may be loaded by another executable program and interpreted to generate instructions in a random access portion of the memory to be executed by a processor. The executable program may be stored in any portion or component of the memory device 720. For example, the memory device 720 may be random access memory (RAM), read only memory (ROM), flash memory, a solid state drive, memory card, a hard drive, optical disk, floppy disk, magnetic tape, or any other memory components.

The processor 712 may represent multiple processors and the memory 720 may represent multiple memory units that operate in parallel to the processing circuits. This may provide parallel processing channels for the processes and data in the system. The local interface 718 may be used as a network to facilitate communication between any of the multiple processors and multiple memories. The local interface 718 may use additional systems designed for coordinating communication such as load balancing, bulk data transfer, and similar systems.

While the flowcharts presented for this technology may imply a specific order of execution, the order of execution may differ from what is illustrated. For example, the order of two more blocks may be rearranged relative to the order shown. Further, two or more blocks shown in succession may be executed in parallel or with partial parallelization. In some configurations, one or more blocks shown in the flow chart may be omitted or skipped. Any number of counters, state variables, warning semaphores, or messages might be added to the logical flow for purposes of enhanced utility, accounting, performance, measurement, troubleshooting or for similar reasons.

Some of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more blocks of computer instructions, which may be organized as an object, procedure, or function. Nevertheless, the executables of an identified module need not be physically located together, but may comprise disparate instructions stored in different locations which comprise the module and achieve the stated purpose for the module when joined logically together.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices. The modules may be passive or active, including agents operable to perform desired functions.

The technology described here can also be stored on a computer readable storage medium that includes volatile and non-volatile, removable and non-removable media implemented with any technology for the storage of information such as computer readable instructions, data structures, program modules, or other data. Computer readable storage media include, but is not limited to, RAM, ROM, EEPROM, flash memory or other memory technology, CD-ROM, digital versatile disks (DVD) or other optical storage, magnetic cassettes, magnetic tapes, magnetic disk storage or other magnetic storage devices, or any other computer storage medium which can be used to store the desired information and described technology.

The devices described herein may also contain communication connections or networking apparatus and networking connections that allow the devices to communicate with other devices. Communication connections are an example of communication media. Communication media typically embodies computer readable instructions, data structures, program modules and other data in a modulated data signal such as a carrier wave or other transport mechanism and includes any information delivery media. A "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared, and other wireless media. The term computer readable media as used herein includes communication media.

Reference was made to the examples illustrated in the drawings, and specific language was used herein to describe the same. It will nevertheless be understood that no limitation of the scope of the technology is thereby intended. Alterations and further modifications of the features illustrated herein, and additional applications of the examples as illustrated herein, which would occur to one skilled in the relevant art and having possession of this disclosure, are to be considered within the scope of the description.

Furthermore, the described features, structures, or characteristics may be combined in any suitable manner in one or more examples. In the preceding description, numerous specific details were provided, such as examples of various configurations to provide a thorough understanding of examples of the described technology. One skilled in the relevant art will recognize, however, that the technology can be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements can be devised without departing from the spirit and scope of the described technology.

What is claimed is:

1. A method for incorporating statistical strength from neighboring voxels in an fMRI image, comprising:
   receiving an fMRI image of a human organ as captured by an MRI machine and the fMRI image includes statistical values for voxels in order to detect changes associated with blood flow representing organ activity;
   upsampling the statistics of the fMRI image to a larger coordinate size;
   resampling the statistical values of the fMRI image to improve the statistical strength for target voxels in the fMRI by identifying strong statistical values in neighboring voxels in a defined neighborhood of the target voxels and improving statistical values of the target voxels using the strong statistical values;
   integrating the statistics of the fMRI image in a region of interest identified for the human organ to improve data values of the target voxels while retaining regional boundaries; and
   displaying the fMRI image with improved data values of the target voxels in a display such that the fMRI image is overlaid over an anatomical image of the human organ.

2. The method as in claim 1, further comprising:
   identifying the anatomical image of the human organ.

3. The method as in claim 1, further comprising modifying the target voxel by adjusting the statistical value of the target voxels by determining that voxels in a neighborhood of interest are statistically likely to be related to the target voxels.

4. The method as in claim 1, modifying the target voxels by increasing the statistical value of target voxels after identifying strong statistical values with increased statistical values in neighboring voxels using cubic interpolation.

5. The method as in claim 1, modifying the target voxels by decreasing the value of selected voxels after identifying strong statistical values with decreased statistical values in neighboring voxels using cubic interpolation.

6. The method as in claim 1, further comprising modifying the value of target voxels using values of 64 neighbor voxels in three dimensions.

7. The method as in claim 1, further comprising resampling statistics of the fMRI image using cubic interpolation of the voxels in three dimensions in a region near each of the target voxels.

8. The method as in claim 1, further comprising applying a separate color to individual statistical value groups in the fMRI image.

9. The method as in claim 1, further comprising displaying the fMRI image for medical diagnostic purposes.

10. The method as in claim 1, further comprising:
    comparing a subject fMRI image against reference group data; and
    reporting when a subject fMRI image is at least one standard deviation from an average of the reference group data.

11. A method for incorporating statistical strength into voxels in an fMRI image, comprising:
    receiving an fMRI image of a human brain as captured by an MRI machine, wherein the fMRI images having voxels with statistical values representing brain activity by identifying changes associated with blood flow;
    resampling statistical value for target voxels of the fMRI image to improve the statistical strength for target voxels in the fMRI image by using statistics of selected voxels in a defined neighborhood;
    upsampling the statistics of the fMRI image to a coordinate size;
    integrating the statistics of the fMRI image in a region of interest identified for the human brain;
    identifying an anatomical image of the brain;
    displaying, in a display device, the fMRI image, which has been upsampled, such that the fMRI image is overlaid over the anatomical image of the brain; and
    indicating when a subject fMRI image has been calculated as having a statistically significant deviation from an average of reference group data.

12. The method as in claim 11, further comprising modifying the target voxels by adjusting the value of the selected voxels by determining that selected voxels in a neighborhood of interest are statistically likely to be related to the selected voxels.

13. The method as in claim 11, further comprising modifying the selected voxels by increasing the value of selected voxels by determining that voxels in a neighborhood of interest are statistically likely to increase the value of the selected voxels.

14. The method as in claim 11, modifying the selected voxels by decreasing the value of selected voxels by determining that voxels in a neighborhood of interest are statistically likely to decrease the value of the selected voxels.

15. The method as in claim 11, further comprising resampling the statistics of the fMRI by modifying the value of selected voxels in response to groups of statistical values for neighbor voxels.

16. The method as in claim 15, further comprising modifying the value of selected voxels using values of 64 neighbor voxels in three dimensions.

17. The method as in claim 11, further comprising resampling the statistical values of the fMRI image using cubic interpolation of the voxels in a region near each of the target voxels.

18. The method as in claim 11, further comprising applying a plurality of colors to statistical value groups in the fMRI image.

19. A system for capturing an fMRI image of a human brain to represent brain activity by detecting changes associated with blood flow, the system comprising:
    one or more processors;
    a display device;
    memory; and
    one or more programs stored in the memory, the one or more programs comprising instructions that, when executed by the one or more processors, cause the system to:
    resample statistics of the fMRI image to improve statistical strength for target voxels in the fMRI from selected voxels in a defined neighborhood;
    upsample the statistics of the fMRI image to a larger coordinate size;
    integrate the statistics of the fMRI image in a region of interest identified for the human brain to;
    identify an anatomical image of the brain; and
    overlay the fMRI image that has been upsampled over the anatomical image of the brain to be displayed in the display device.

20. The system as in claim 19, further comprising resampling statistical values of the fMRI image using cubic interpolation of the voxels in a region near each of the target voxels.

* * * * *